(12) United States Patent
Wang

(10) Patent No.: US 7,572,585 B2
(45) Date of Patent: *Aug. 11, 2009

(54) ENZYMATIC LABELING OF RNA

(75) Inventor: Hui Wang, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 366 days.

This patent is subject to a terminal disclaimer.

(21) Appl. No.: 11/496,831

(22) Filed: Jul. 31, 2006

(65) Prior Publication Data

US 2008/0026382 A1    Jan. 31, 2008

(51) Int. Cl.
*C12Q 1/68* (2006.01)
*C12P 19/34* (2006.01)

(52) U.S. Cl. .......................... 435/6; 435/91.1; 435/91.2

(58) Field of Classification Search ....................... None
See application file for complete search history.

(56) References Cited

U.S. PATENT DOCUMENTS

| | | | |
|---|---|---|---|
| 4,661,450 | A | 4/1987 | Kempe et al. |
| 5,659,025 | A | 8/1997 | Engels et al. |
| 5,985,567 | A | 11/1999 | Rampal |
| 6,218,142 | B1 | 4/2001 | Wassenegger et al. |
| 2004/0086914 | A1* | 5/2004 | Cole et al. ..................... 435/6 |
| 2005/0059005 | A1* | 3/2005 | Tuschl et al. ................... 435/6 |
| 2005/0075492 | A1* | 4/2005 | Chen et al. ................. 536/23.1 |
| 2005/0123952 | A1* | 6/2005 | Griffey et al. .................. 435/6 |
| 2007/0026411 | A1* | 2/2007 | Wang et al. ..................... 435/6 |
| 2007/0212697 | A1* | 9/2007 | Sampson et al. ................ 435/6 |
| 2008/0272006 | A1 | 11/2008 | Gao |

OTHER PUBLICATIONS

Romaniuk et al., "Joining of RNA Molecules with RNA Ligase," Methods in Enzymology, 1983, vol. 100, pp. 52-59.*

Cobianchi, F., et al. Enzymes for modifying and labeling DNA and RNA. Methods in Enzymology. 1987, vol. 152, pp. 94-110.

Cole, K., et al. Direct labeling of RNA with multiple biotins allows sensitive expression profiling of acute leukemia class predictor genes. Nucleic Acids Research. 2004, vol. 32, No. 11, pp. e86.

England, T., et al. Enzymatic oligoribonucleotide synthesis with T4 RNA ligase. Biochemistry. 1978, vol. 17, No. 11, pp. 2069-2076.

Liang, R., et al. An oligonucleotide microarray for microRNA expression analysis based on labeling RNA with quantum dot and nanogold probe. Nucleic Acids Research. 2005, vol. 33, No. 2, pp. e17.

McLaughlin, L., et al. Donor activation in the T4 RNA ligase reaction. Biochemistry. 1985. vol. 24, pp. 267-273.

Middleton, T., et al. Synthesis and purification of oligoribonucleotides using T4 RNA ligase and reverse-phase chromatography. Analytical Biochemistry. 1985, vol. 144, pp. 110-117.

Nelson, P.,et al. Microarray-based, high-throughput gene expression profiling of microRNAs. Nature Methods. 2004, vol. 1, No. 2, pp. 155-161.

Ohtsuka, E., et al. Comparison of substrate case sequences for RNA ligase reactions in the synthesis of a tetradecanucleotide corresponding to bases 21-34 of *E. coli* tRNAfMet 1. Nucleic Acids Research. 1980, vol. 8, No. 17, pp. 3909-3916.

Romaniuk, E., et al. The effect of acceptor oligoribonucleotide sequence of the T4 RNA ligase reaction. European Journal of Biochemistry. 1982, vol. 125, pp. 639-643.

Tessier, D., et al. Ligation of single-stranded oligodeoxyribonucleotides by T4 RNA ligase. Analytical Biochemistry. 1986, vol. 158, pp. 171-178.

Thomson, J., et al. A custom microarray platform for analysis of microRNA gene expression. Nature Methods. 2004, vol. 1, No. 1, pp. 47-53.

Yin, J., et al. Identifying expression of new small RNAs by microarrays. Methods. 2007, vol. 43, pp. 123-130.

* cited by examiner

*Primary Examiner*—Young J Kim

(57) ABSTRACT

Methods are described in which a sample containing RNA is contacted with an enzyme having an RNA ligation activity in the presence of a labeled substrate to provide labeled RNA. Methods of performing an array analysis of a labeled RNA sample are also described.

13 Claims, 3 Drawing Sheets

Fig._2

ENZYMATIC LABELING OF RNA

FIELD OF THE INVENTION

The invention relates generally to methods of biochemical analysis. More specifically, the invention relates to providing a method of attaching an observable label to RNA.

BACKGROUND OF THE INVENTION

Straightforward and reliable methods for simultaneously analyzing several constituents of a complex sample are extremely desirable. Polynucleotide arrays (such as DNA or RNA arrays) are known and are used, for example, as diagnostic or screening tools. Such arrays include regions of usually different sequence polynucleotides ("capture agents") arranged in a predetermined configuration on a support. The arrays are "addressable" in that these regions (sometimes referenced as "array features") have different predetermined locations ("addresses") on the support of array. The polynucleotide arrays typically are fabricated on planar supports either by depositing previously obtained polynucleotides onto the support in a site specific fashion or by site specific in situ synthesis of the polynucleotides upon the support. After depositing the polynucleotide capture agents onto the support, the support is typically processed (e.g., washed and blocked for example) and stored prior to use.

In use, an array is contacted with a sample or labeled sample containing analytes (typically, but not necessarily, other polynucleotides) under conditions that promote specific binding of the analytes in the sample to one or more of the capture agents present on the array. Thus, the arrays, when exposed to a sample, will undergo a binding reaction with the sample and exhibit an observed binding pattern. This binding pattern can be detected upon interrogating the array. For example all target polynucleotides (for example, DNA) in the sample can be labeled with a suitable label (such as a fluorescent compound), and the label then can be accurately observed (such as by observing the fluorescence pattern) on the array after exposure of the array to the sample. Assuming that the different sequence polynucleotides were correctly deposited in accordance with the predetermined configuration, then the observed binding pattern will be indicative of the presence and/or concentration of one or more components of the sample. Techniques for scanning arrays are described, for example, in U.S. Pat. No. 5,763,870 and U.S. Pat. No. 5,945,679. Still other techniques useful for observing an array are described in U.S. Pat. No. 5,721,435.

There has been great interest in the analysis of small RNAs, such as short interfering RNAs (siRNAs), microRNAs (miRNA), tiny non-codingRNAs (tncRNA) and small modulatory RNA (smRNA), since the discovery of siRNA biological activity over a decade ago. See Novina et al., Nature 430: 161-164 (2004). Even though the functions of most discovered miRNAs remain a mystery, it has become clear that they exist in abundance in plants and animals, with up to tens of thousands of copies per cell. In the fruit fly, 78 have been identified, and over 300 have been identified in human (see the public database accessible via the website accessed by typing "www" followed by ".sanger.ac.uk/cgi-bin/Rfam/mirna/browse.pl" into the address bar of a typical internet browser). The levels of individual miRNAs seem to vary with developmental stages and tissue types. The level of fluctuation may be correlated with phenotype, mRNA levels, or protein levels for better biological insight. Thus quantitative measurements of miRNA may be of great importance. Further, viral miRNAs have been identified and may play a role in latency (see Pfeffer et al., Science, 304: 734-736 (2004)), making the detection and quantification of miRNAs a potentially valuable diagnostic tool.

Analytic methods employing polynucleotide arrays have been used for investigating these small RNAs, e.g. miRNAs have become a subject of investigation with microarray analysis. See, e.g., Liu et al., Proc. Nat'l Acad. Sci. USA, 101: 9740-9744 (2004); Thomson et al., Nature Methods, 1: 1-7 (2004); and Babak et al., RNA, 10: 1813-1819 (2004). Methods of labeling RNAs are of interest for use in array analysis of RNA to provide an observable label used in interrogating the array. In the study of Liu et al., the miRNA was transcribed into DNA with a biotin-labeled primer. This primer was subsequently labeled with streptavidin-linked Alexa dye prior to array hybridization. This method is susceptible to any reverse-transcriptase reaction bias. Further, the streptavidin-dye as well as streptavidin-biotin-RNA stochiometry may be difficult to quantify. In the study of Thomson et al., the miRNA was directly labeled with 5'-phosphate-cytidyl-uridyl-Cy3-3' using T4 RNA ligase. This reaction is sensitive to the acceptor sequence. See England et al., Biochemistry, 17: 2069-2776 (1978). In the study of Babak et al (4), the miRNA was labeled with Ulysis Alexa Fluor system, which reacts with guanine residue (G) of RNA. Since different miRNAs do not have uniform G content, this method is not quantitative.

Thus, there is a continuing need for methods of labeling RNA with an observable label. Such methods may be used in conjunction with analytical methods based on observing the label, such as array-based analysis of polynucleotides.

SUMMARY OF THE INVENTION

The invention thus relates to novel methods for labeling RNA in a sample. In typical embodiments, a RNA sample is first heated to at least about 70° C. in a solution containing at least about 35% DMSO and then cooled to below about 10° C. The RNA sample is then contacted with an enzyme having an RNA ligation activity in the presence of a labeled substrate. This is done under conditions sufficient to result in coupling of the labeled substrate to the RNA in the RNA sample to provide labeled RNA, the conditions including a DMSO concentration in the range from about 20% to about 30%. The labeled substrate includes a nucleotide moiety having a terminal 3'-phosphate group and an observable label moiety attached to the nucleotide moiety via a linking group bound to the terminal 3'-phosphate group. In particular embodiments, the RNA sample is a mixed RNA sample, and the method results in labeled RNA that has reduced sequence bias.

Methods of performing an array analysis of a mixed RNA sample are also taught herein. In certain embodiments, the invention provides a method of performing an array analysis wherein the method includes labeling the RNA in the mixed RNA sample to provide labeled mixed RNA. The labeled mixed RNA is then contacted with an array under conditions sufficient to provide for specific binding of labeled mixed RNA to the array. The array typically is then interrogated to provide data on binding of RNA in the sample to the array.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods particularly pointed out in the appended claims.

BRIEF DESCRIPTION OF THE DRAWINGS

These and other features of the invention will be understood from the description of representative embodiments of the method herein and the disclosure of illustrative compositions and apparatus for carrying out the method, taken together with the Figures, wherein FIG. 1 schematically illustrates embodiments of the present invention.

DETAILED DESCRIPTION

Figure 1:
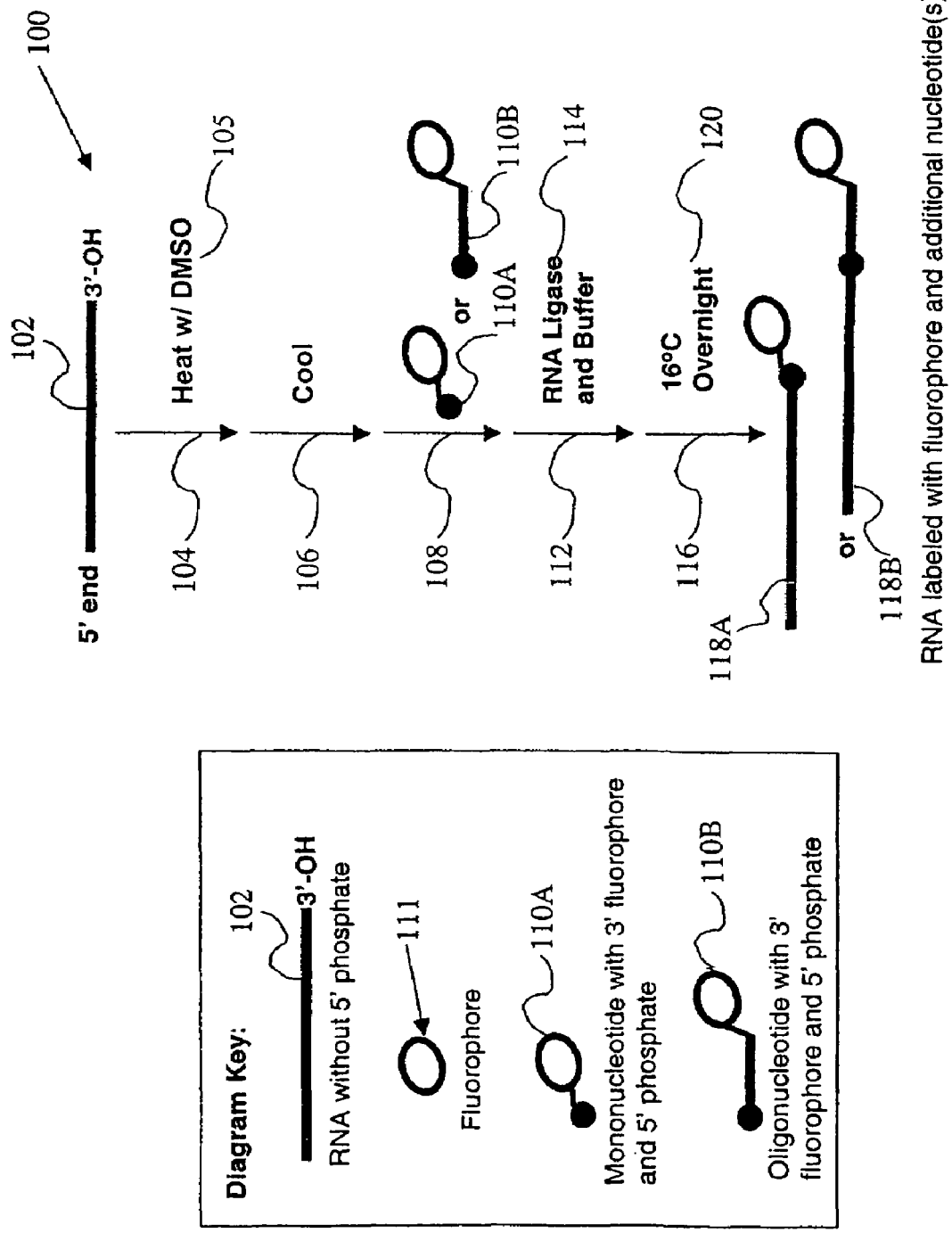

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an insoluble support" includes a plurality of insoluble supports. Similarly, reference to "an RNA" includes a plurality of different identity (sequence) RNA species.

Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. In this specification and in the claims that follow, reference will be made to a number of terms that shall be defined to have the following meanings unless a contrary intention is apparent.

An "oligonucleotide" is a molecule containing from 2 to about 100 nucleotide subunits. The term "nucleic acid" and "polynucleotide" are used interchangeably herein to describe a polymer of any length composed of nucleotides, e.g., deoxyribonucleotides or ribonucleotides, or compounds produced synthetically (e.g., PNA as described in U.S. Pat. No. 5,948, 902 and the references cited therein) which can hybridize with naturally occurring nucleic acids in a sequence specific manner analogous to that of two naturally occurring nucleic acids, e.g., can participate in Watson-Crick base pairing interactions.

A "nucleotide" refers to a sub-unit of a nucleic acid (whether DNA or RNA or analogue thereof) which includes a phosphate group, a sugar group and a nitrogen containing base, as well as analogs of such sub-units. A "nucleoside" references a nucleic acid subunit including a sugar group and a nitrogen containing base, as well as analogs of such sub-units. Additional modification to the nucleoside (or nucleotide) may be necessary depending on the intended use of the nucleoside (or nucleotide), and such modifications are well known. A "nucleoside moiety" refers to a molecule having a sugar group and a nitrogen containing base (as in a nucleoside) as a portion of a larger molecule, such as in a polynucleotide, oligonucleotide, or nucleoside phosphoramidite.

A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer. The terms "nucleoside" and "nucleotide" are intended to include those moieties that contain not only the known purine and pyrimidine bases, but also other heterocyclic bases, such as modified purine and pyrimidine bases. Such modifications include methylated purines or pyrimidines, acylated purines or pyrimidines, alkylated riboses or other heterocycles. Such modifications include, e.g., diaminopurine and its derivatives, inosine and its derivatives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural (not usually occurring in nature) nucleotides, unnatural nucleotide mimetics such as 2'-modified nucleosides, peptide nucleic acids, oligomeric nucleoside phosphonates, and any polynucleotide that has added substituent groups, such as protecting groups or linking moieties.

"Moiety" and "group" are used to refer to a portion of a molecule, typically having a particular functional or structural feature, e.g. a linking group (a portion of a molecule connecting two other portions of the molecule), or an ethyl moiety (a portion of a molecule with a structure closely related to ethane). A moiety is generally bound to one or more other moieties to provide a molecular entity. As a simple example, a hydroxyl moiety bound to an ethyl moiety provides an ethanol molecule. At various points herein, the text may refer to a moiety by the name of the most closely related structure (e.g. an oligonucleotide moiety may be referenced as an oligonucleotide, a mononucleotide moiety may be referenced as a mononucleotide). However, despite this seeming informality of terminology, the appropriate meaning will be clear to those of ordinary skill in the art given the context, e.g. if the referenced term has a portion of its structure replaced with another group, then the referenced term is usually understood to be the moiety. For example, a mononucleotide moiety is a single nucleotide which has a portion of its structure (e.g. a hydrogen atom, hydroxyl group, or other group) replaced by a different moiety (e.g. a linking group, an observable label moiety, or other group). Similarly, an oligonucleotide moiety is an oligonucleotide which has a portion of its structure (e.g. a hydrogen atom, hydroxyl group, or other group) replaced by a different moiety (e.g. a linking group, an observable label moiety, or other group). "Nucleotide moiety" is generic to both mononucleotide moiety and oligonucleotide moiety.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

Moreover, the term "alkyl" includes "modified alkyl", which references an alkyl group having from one to twenty-four carbon atoms, and further having additional groups, such as one or more linkages selected from ether-, thio-, amino-, phospho-, oxo-, ester-, and amido-, and/or being substituted with one or more additional groups including lower alkyl, aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. Similarly, the term "lower alkyl" includes "modified lower alkyl", which references a group having from one to eight carbon atoms and further having additional groups, such as one or more linkages selected from ether-, thio-, amino-, phospho-, keto-, ester-, and amido-, and/or being substituted with one or more groups including lower alkyl; aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more substituents typically selected from the group consisting of lower alkyl, aryl, aralkyl, lower alkoxy, thioalkyl, hydroxyl, thio, mercapto, amino, imino, halo, cyano, nitro, nitroso, azide, carboxy, sulfide, sulfone, sulfoxy, phosphoryl, silyl, silyloxy, and boronyl; and lower alkyl substituted with one or more groups selected from lower alkyl, alkoxy, thioalkyl, hydroxyl thio, mercapto, amino, imino, halo, cyano, nitro, nitroso, azide, carboxy, sulfide, sulfone, sulfoxy, phosphoryl, silyl, silyloxy, and boronyl. Typical aryl groups contain 1 to 3 fused aromatic rings, and more typical aryl groups contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —(CH2)j-Ar wherein j is an integer in the range of 1 to 24, more typically 1 to 6, and Ar is a monocyclic aryl moiety.

The term "halo" or "halogen" is used in its conventional sense to refer to a chloro, bromo, fluoro or iodo substituent.

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

Hyphens, or dashes, are used at various points throughout this specification to indicate attachment, e.g. where two named groups are immediately adjacent a dash in the text, this indicates the two named groups are attached to each other. Similarly, a series of named groups with dashes between each of the named groups in the text indicates the named groups are attached to each other in the order shown. Also, a single named group adjacent a dash in the text indicates the named group is typically attached to some other, unnamed group. In some embodiments, the attachment indicated by a dash may be, e.g. a covalent bond between the adjacent named groups. In some other embodiments, the dash may indicate indirect attachment, i.e. with intervening groups between the named groups. At various points throughout the specification a group may be set forth in the text with or without an adjacent dash, (e.g. amido or amido-, further e.g. alkyl or alkyl-, yet further e.g. Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g. where a linkage is intended, such as linking groups).

"Optional" or "optionally" means that the subsequently described circumstance may or may not occur, so that the description includes instances where the circumstance occurs and instances where it does not. For example, if a step of a process is optional, it means that the step may or may not be performed, and, thus, the description includes embodiments wherein the step is performed and embodiments wherein the step is not performed (i.e. it is omitted). As another example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

"Bound" may be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. "Free," as used in the context of a moiety that is free, indicates that the moiety is available to react with or be contacted by other components of the solution in which the moiety is a part.

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present and/or determining whether it is present or absent.

The term "mixture", as used herein, refers to a combination of elements, e.g., binding agents or analytes, that are interspersed and not in any particular order. A mixture is homogeneous and not spatially separated into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable. To be specific, an array of ligands, as is commonly known in the art, is not a mixture of ligands because the species of ligands are spatially distinct and the array is addressable.

"Isolated" or "purified" generally refers to isolation of a substance (compound, polynucleotide, protein, polypeptide, polypeptide, chromosome, etc.) such that the substance comprises a substantial portion of the sample in which it resides (excluding solvents), i.e. greater than the substance is typically found in its natural or un-isolated state. Typically, a substantial portion of the sample comprises at least about 5%, at least about 10%, at least about 20%, at least about 30%, at least about 50%, preferably at least about 80%, or more preferably at least about 90% of the sample (excluding solvents). For example, a sample of isolated RNA will typically comprise at least about 5% total RNA, where percent is calculated in this context as mass (e.g. in micrograms) of total RNA in the sample divided by mass (e.g. in micrograms) of the sum of (total RNA+other constituents in the sample (excluding solvent)). Techniques for purifying polynucleotides and polypeptides of interest are well known in the art and include, for example, gel electrophoresis, ion-exchange chromatography, affinity chromatography, flow sorting, and sedimentation according to density. In typical embodiments, one or more of the sample, the enzyme having an RNA ligation activity, and the labeled substrate is in isolated form; more typically, all three are obtained in isolated form prior to use in the present methods.

The term "sample" as used herein relates to a material or mixture of materials, typically, although not necessarily, in fluid form, containing one or more components of interest. A mixed RNA sample includes a plurality (e.g. at least 10, at least 20, at least 50, at least 100, at least 200, or more, up to 1000 or more, e.g. up to 10,000 or more) of different species of RNA in the sample. In other words, a mixed RNA sample includes RNA molecules that have many different sequences (identities), such as may typically be obtained by isolating RNA from a biological source.

The term "analyte" is used herein to refer to a known or unknown component of a sample. In certain embodiments of the invention, an analyte may specifically bind to a capture agent on a support surface if the analyte and the capture agent are members of a specific binding pair. In general, analytes are typically RNA or other polynucleotides. Typically, an "analyte" is referenced as a species in a mobile phase (e.g., fluid), to be detected by a "capture agent" which, in some embodiments, is bound to a support, or in other embodiments, is in solution. However, either of the "analyte" or "capture agent" may be the one which is to be evaluated by the other (thus, either one could be an unknown mixture of components of a sample, e.g., polynucleotides, to be evaluated by binding with the other). A "target" references an analyte.

The term "capture agent" refers to an agent that binds an analyte through an interaction that is sufficient to permit the agent to bind and concentrate the analyte from a homogeneous mixture of different analytes. The binding interaction may be mediated by an affinity region of the capture agent. Representative capture agents include polypeptides and polynucleotides, for example antibodies, peptides, or fragments of double stranded or single-stranded DNA or RNA may employed. Capture agents usually "specifically bind" one or more analytes.

The term "specific binding" refers to the ability of a capture agent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold). In certain embodiments, the binding constant of a capture agent and analyte is greater than $10^6$ $M^{-1}$, greater than $10^7$ $M^{-1}$, greater than $10^8$ $M^{-1}$, greater than $10^9$ $M^{-1}$, greater than $10^{10}$ $M^{-1}$, usually up to about $10^{12}$ $M^{-1}$, or even up to about $10^{15}$ $M^{-1}$.

The term "stringent assay conditions" as used herein refers to conditions that are compatible to produce binding pairs of nucleic acids, e.g., capture agents and analytes, of sufficient complementarity to provide for the desired level of specificity in the assay while being incompatible to the formation of binding pairs between binding members of insufficient complementarity to provide for the desired specificity. Stringent assay conditions are the summation or combination (totality) of both hybridization and wash conditions.

A "stringent hybridization" and "stringent hybridization wash conditions" in the context of nucleic acid hybridization (e.g., as in array, Southern or Northern hybridizations) are sequence dependent, and are different under different experimental conditions. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO4, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions may affect the degree to which nucleic acids are specifically hybridized to complementary capture agents. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 1 to about 20 minutes; or, multiple washes with a solution with a salt concentration of about 0.1×SSC containing 0.1% SDS at 20 to 50° C. for 1 to 15 minutes; or, equivalent conditions. Stringent conditions for washing can also be, e.g., 0.2×SSC/0.1% SDS at 42° C. In instances wherein the nucleic acid molecules are deoxyoligonucleotides (i.e., oligonucleotides), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions. See, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.

A specific example of stringent assay conditions is rotating hybridization at a temperature of about 55° C. to about 70° C. in a salt based hybridization buffer with a total monovalent cation concentration of 1.5M (e.g., as described in U.S. patent application Ser. No. 09/655,482 filed on Sep. 5, 2000, the disclosure of which is herein incorporated by reference) followed by washes of 0.5×SSC and 0.1×SSC at room temperature and 37° C.

Stringent hybridization conditions may also include a "prehybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA or with random sequence synthetic oligonucleotides (e.g. 25-mers), or the like.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The term "pre-determined" refers to an element whose identity is known prior to its use. For example, a "pre-determined analyte" is an analyte whose identity is known prior to any binding to a capture agent. An element may be known by name, sequence, molecular weight, its function, or any other attribute or identifier. In some embodiments, the term "analyte of interest", i.e., a known analyte that is of interest, is used synonymously with the term "pre-determined analyte".

The term "array" encompasses the term "microarray" and refers to an ordered array of capture agents for binding to aqueous analytes and the like. An "array" includes any two-dimensional or substantially two-dimensional (as well as a three-dimensional) arrangement of spatially addressable regions (i.e., "features") containing capture agents, particularly polynucleotides, and the like. Any given support may carry one, two, four or more arrays disposed on a surface of a support. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 100 cm$^2$, 20 cm$^2$ or even less than 10 cm$^2$, e.g., less than about 5 cm$^2$, including less than about 1 cm$^2$, less than about 1 mm$^2$, e.g., 100 µm$^2$, or even smaller. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of the same or different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Arrays can be fabricated by depositing (e.g., by contact- or jet-based methods) either precursor units (such as nucleotide or amino acid monomers) or pre-synthesized capture agent. An array is "addressable" when it has multiple regions of different moieties (e.g., different capture agent) such that a region (i.e., a "feature" or "spot" of the array) at a particular predetermined location (i.e., an "address") on the array will detect a particular sequence. An "array layout" refers to one or more characteristics of the features, such as feature positioning on the support, one or more feature dimensions, and an indication of a moiety at a given location. "Interrogating" the array refers to obtaining information from the array, especially information about analytes binding to the array. "Hybridization assay" references a process of contacting an array with a mobile phase containing analyte. An "array support" refers to an article that supports an addressable collection of capture agents.

"Complementary" references a property of specific binding between polynucleotides based on the sequences of the polynucleotides. As used herein, polynucleotides are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C. "Complementary" includes embodiments in which there is an absolute sequence complementarity, and also embodiments in which there is a substantial sequence complementarity. "Absolute sequence complementarity" means that there is 100% sequence complementarity between a first polynucleotide and a second polynucleotide, i.e. there are no insertions, deletions, or substitutions in either of the first and second polynucleotides with respect to the other polynucleotide (over the complementary region). Put another way, every base of the complementary region may be paired with its complementary base, i.e. following normal base-pairing rules. "Substantial sequence complementarity" permits one or more relatively small (less than 10 bases, e.g. less than 5 bases, typically less than 3 bases, more typically a single base) insertions, deletions, or substitutions in the first and/or second polynucleotide (over the complementary region) relative to the other polynucleotide. The region that is complementary between a first polynucleotide and a second polynucleotide (e.g. a target analyte and a capture agent) is typically at least about 10 bases long, more typically at least about 15 bases long, still more typically at least about 20 bases long, or at least about 25 bases long. In various typical embodiments, the region that is complementary between a first polynucleotide and a second polynucleotide (e.g. target analyte and a capture agent) may be up to about 200 bases long, or up to about 120 bases long, up to about 100 bases long, up to about 80 bases long, up to about 60 bases long, or up to about 45 bases long.

"Upstream" as used herein refers to the 5' direction along a polynucleotide, e.g. an RNA molecule. "Downstream" refers to the 3' direction along the polynucleotide. Hence, a label downstream of an analyte is located at (or is bound to) a nucleotide moiety that is located in the 3' direction from the analyte, e.g. bound to the 3' end of the analyte. Similarly, an "upstream label" references a label that is located at (or is bound to) a nucleotide moiety that is located in the 5' direction from the analyte, e.g. bound to the 5' end of the analyte. "3'-" and "5'-" have their conventional meaning as known in the art. A 5'-phosphate is a phosphate group located at the 5'-end of a polynucleotide. A 3'-hydroxyl is a hydroxyl group located at the 3'-end of a polynucleotide. Similarly, a 3'-phosphate is a phosphate group located at the 3'-end of a polynucleotide. As an example, FIG. 1 illustrates a method in accordance with the present invention for downstream labeling of an analyte. If the polynucleotide is double stranded, one of the strands is selected as the reference strand, e.g. the strand that is labeled, or the strand that is not labeled (or some other criteria or feature of the strand may be used to designate one strand as the reference strand).

Accordingly, in one embodiment of the present invention, a method of labeling RNA in a sample is provided. In typical embodiments, the method includes heating a RNA sample to at least about 70° C. in a solution containing at least about 35% DMSO, and then cooling the RNA sample to below about 10° C. The method includes contacting the RNA sample with an enzyme having an RNA ligation activity in the presence of a labeled substrate under conditions sufficient to result in coupling of the labeled substrate to the RNA in the sample to provide labeled RNA, the conditions including a DMSO concentration in the range from about 20% to about 30%. The labeled substrate includes a nucleotide moiety having a terminal 3'-phosphate group and an observable label moiety attached to the nucleotide moiety via a linking group bound to the terminal 3'-phosphate group.

The sample may be any RNA sample, typically a sample containing RNA that has been isolated from a biological source, e.g. any plant, animal, yeast, bacterial, or viral source, or a non-biological source, e.g. chemically synthesized. In typical embodiments, the sample is a sample of mixed RNA. A mixed RNA sample includes a plurality (e.g. at least 10, at least 20, at least 50, at least 100, at least 200, or more, up to 1000 or more, e.g. up to 10,000 or more) of different species of RNA in the sample. In other words, a mixed RNA sample includes RNA molecules that have many different sequences (identities), such as may typically be obtained by isolating RNA from a biological source. In particular embodiments, the RNA sample is a mixed RNA sample, wherein the mixed RNA sample includes a plurality of different RNAs (called "member RNAs" herein to denote their presence in the mixed RNA sample). The different member RNAs are characterized as having different primary and secondary structures that may affect the activity of the enzyme having an RNA ligation activity, such that the rate or extent of a ligation reaction involving the different member RNAs may be sequence dependent (i.e. dependent on the nucleotide sequence of the individual member RNAs). In certain embodiments, the mixed RNA sample include a first plurality of different member RNAs having a 3' terminal U, a second plurality of different member RNAs having a 3' terminal G, a third plurality of different member RNAs having a 3' terminal A, and a fourth plurality of different member RNAs having a 3' terminal C. When labeled using a labeling method that provides low sequence bias in labeling the RNA, the result is labeled RNA having low sequence bias (despite the different 3'-terminal nucleotides).

In particular embodiments, the sample includes small RNAs, especially RNAs less than about 500 bases long, e.g. less than about 400 bases long, less than about 300 bases long, less than about 200 bases long, or less than about 100 bases long. In particular embodiments, the sample includes one or more short RNAs, such as e.g. short interfering RNAs (siRNAs), microRNAs (miRNA), tiny non-coding RNAs (tncRNA) and small modulatory RNA (smRNA). See Novina et al., Nature 430: 161-164 (2004). In particular embodiments, the sample includes isolated small RNAs, e.g. the sample results from an isolation protocol for small RNA such as one or more of those listed in this paragraph. In certain embodiments, the small RNA targets may include isolated miRNAs, such as those described in the literature and in the public database accessible via the website located at >>http://www.sanger.ac.uk/cgi-bin/Rfam/mirna/browse.pl<<. In particular embodiments, the sample includes isolated small RNAs, e.g. the sample results from an isolation protocol for small RNA, especially RNAs less than about 500 bases long, e.g. less than about 400 bases long, less than about 300 bases long, less than about 200 bases long, less than about 100 bases long, or less than about 50 bases long. A sample that includes isolated small RNA from a biological source will usually be a mixed RNA sample, as it will usually include many different small RNAs.

As mentioned above, in typical embodiments in accordance with the present invention, the method optionally includes an initial heating of the RNA sample followed by a cooling of the RNA sample. The conditions for heating of the RNA sample typically will include a temperature of at least 70° C. (e.g. at least 80° C., at least 90° C., at least 95° C.) and up to about 100° C. (or more, e.g. up to 110° C., up to 120° C.); and during the heating step the RNA sample typically comprises at least about 35% DMSO (e.g. at least 40% DMSO), up to about 45%, 50%, 60%, 70%, 80%, or more DMSO. The RNA sample solution is heated for a time sufficient to denature secondary structures formed by the RNA in the RNA sample, typically for a time period of at least 15 seconds, e.g. at least 30 seconds, at least 1 minute, at least 2 minutes, wherein the time period typically is less than about 30 minutes, e.g. less than 15 minutes, less than 10 minutes, less than 5 minutes, although in some embodiments the time period may be outside the given ranges, e.g. less than 15 seconds or more than 30 minutes. After the indicated time period of heating the RNA sample is completed, the RNA sample is then quickly cooled to a temperature below about 10° C. (e.g. at a temperature in the range from about −5° C. to about 10° C., e.g. in the range from about −5° C. to about 5° C.), e.g. vials containing the RNA sample may be placed on an ice bath or cooling block. In typical embodiments, the RNA sample is maintained at the cool temperature for at least 1 minute, more typically at least 2 minutes, e.g. at least 5 minutes, and up to 15 minutes or more, e.g. up to 30 minutes or more, such as until the RNA sample is needed for the next steps in the method. In certain embodiments, the heating and cooling steps are optional and may be omitted.

The dimethylsulfoxide (DMSO) concentration is calculated as volume (e.g. in milliliters) of DMSO divided by total volume (e.g. in milliliters) of the solution containing the DMSO. This quantity is typically cast as a percentage by multiplying by 100%. For example, the DMSO concentration may be in a range of 35% to about 70%, calculated as the volume of DMSO in the RNA sample solution, divided by the total volume of the solution, and then multiplying by 100%. The other components present in the resulting solution will typically be water, buffer components, salt, RNA, although other components may also be present.

As mentioned above, in typical embodiments, the method includes contacting the RNA sample with an enzyme having an RNA ligation activity in the presence of a labeled substrate under conditions sufficient to result in coupling of the labeled substrate to the RNA in the sample to provide labeled RNA, the conditions including a DMSO concentration in the range from about 20% to about 30%.

The enzyme having an RNA ligation activity is typically any RNA ligase enzyme, although other enzymes capable of coupling the labeled substrate to the RNA may be used. In particular embodiments, the enzyme having an RNA ligation activity is capable of coupling a nucleotide (or oligonucleotide, or RNA) having a 5' phosphate to an oligonucleotide having a 3' hydroxyl. Exemplary enzymes include T4 RNA ligase available from Amersham/Pharmacia company, ThermoPhage™ RNA ligase II (available from Prokaria LTD, Iceland), or other available RNA ligase enzymes known to be capable of coupling a nucleotide (or oligonucleotide, or RNA) having a 5' phosphate to an oligonucleotide having a 3' hydroxyl. In certain embodiments, the enzyme may be selected from yeast poly A polymerase, E. coli poly A polymerase, or terminal transferase (each of which is available from Amersham/Pharmacia). The enzyme having an RNA ligation activity typically is capable performing the coupling when the nucleotide (or oligonucleotide) having a 5'phosphate includes a label. Selection of the enzyme having an RNA ligation activity will typically be based on availability of the enzyme and activity of the enzyme under the desired reaction conditions for the coupling (e.g. temperature, pH, ionic strength, source of RNA and/or labeled substrate, structural feature of RNA and/or labeled substrate, concentration of RNA and/or labeled substrate, presence of other materials (e.g. contaminants, salt, surfactant, other solvents) etc.)

The coupling reaction is conducted under conditions sufficient to result in coupling. The conditions of the coupling reaction will generally be selected with regard to the known (previously described) conditions for use of the particular enzyme chosen for use in the methods of the invention, with the specific modifications described herein. As already indicated, the DMSO of the reaction mixture for the coupling reaction will be in the range of 20% to 30%. Other experimental parameters may be selected based on known ranges for the experimental parameters or determined through routine experimentation based on, e.g. efficacy of the labeling reaction. Such other experimental parameters may include, e.g. temperature, pH, ionic strength, source of RNA and/or labeled substrate, structural feature of RNA and/or labeled substrate, concentration of RNA and/or labeled substrate, presence of other materials (e.g. contaminants, salt, surfactant, other solvents) etc.

Early work reported by Uhlenbeck et al. characterized the reaction catalysed by T4 RNA ligase. (See, e.g. England & Uhlenbeck, Biochemistry (1978) 17: 2069.) This early work by Uhlenbeck et al. established that the minimal substrates for the ligation reaction catalysed by T4 RNA ligase reaction are a trinucleoside diphosphate acceptor and a nucleoside 3',5'-bisphosphate donor. This early work also established that the yield of the ligation reaction was dependent on the nucleotide sequence of the acceptor. In reactions employing purified substrates, the yields ranged from 11% to 100%, depending on the nucleotide sequence of the acceptor. This "sequence-bias" of the ligation reaction results in different acceptor substrates having varying yields in the ligation reaction. "Sequence-bias" references a tendency for one substrate to undergo ligation at a higher or lower yield than other substrates in a reaction mixture based on the nucleotide sequence and/or secondary structure of the substrate. In general, however, a desirable aspect of a labeling reaction is that the labeling reaction provides for quantitative interpretation of the results. If the labeling reaction is subject to a substantial amount of sequence bias, the relative amounts of RNAs labeled by the labeling reaction will be altered, decreasing the ability to quantitatively determine relationships between member RNAs in a mixed RNA sample. If a mixed RNA sample containing many different member RNAs undergoes a ligation reaction that provides for low sequence bias, the resulting collection of labeled member RNAs is said to have "low sequence bias".

In particular embodiments, the method of the present invention provides for low sequence bias in the labeling reaction, and thus provides for labeling mixed RNA samples to provide labeled mixed RNA samples having low sequence bias. In this context, a reaction with "low sequence bias"

proceeds (under a given set of conditions) with a yield that is similar (within about 25%) for most of the member RNAs (e.g. at least 60%, at least 70%, at least 80%) in the mixed RNA sample. The product of the labeling reaction on a mixed RNA sample will be a labeled mixed RNA sample, wherein the individual components of the labeled mixed RNA sample are labeled to a substantially similar extent. The distribution of labeled RNAs substantially represents (plus or minus about 25%) the distribution of RNAs present in the initial sample. That is, the proportion of each given member labeled RNA in the total labeled RNA is substantially the same as the proportion of the corresponding (unlabeled) member RNA in the total initial sample of mixed RNA. In this context "substantially the same" means less than about 25% difference in the proportions, e.g. less than about 20%, less than about 15%, less than about 10%, less than about 5%.

Expressed as an equation,

$$RNA(n)/RNA_{total} \approx RNA(n)\text{-Label}/(RNA\text{-Label})_{total}$$

Wherein

RNA(n) is a given member RNA in the initial sample;

$RNA_{total}$ is the total initial sample of mixed RNA;

RNA(n)–Label is the labeled member RNA (after the labeling reaction);

(RNA–Label)$_{total}$ is the total labeled RNA (after the labeling reaction).

The labeled substrate includes a nucleotide moiety having a terminal 3'-phosphate group and an observable label moiety attached to the nucleotide moiety via a linking group bound to the terminal 3'-phosphate group. The nucleotide moiety is typically a mononucleotide moiety or an oligonucleotide moiety. In particular embodiments, the nucleotide moiety is less than about 100 bases long. In certain embodiments, the nucleotide moiety will be less than 50 bases long, e.g. less than 40 bases long, less than 30 bases long, less than 20 bases long. In some embodiments, the nucleotide moiety will be 1, 2, 3, 4, 5, or 6 bases long. The nucleotide moiety may typically have any desired sequence or even an unknown sequence. In certain embodiments, a plurality of labeled substrates may be used in the same reaction (e.g. a plurality of nucleotide moieties, each having a different sequence, each having an observable label moiety attached), thereby resulting in ligating one of a plurality of nucleotide moieties to each molecule of RNA.

In particular embodiments, the labeled substrate has the structure (I):

Q1-Nuc-Q2-Lnk-Lbl     (I)

wherein:

Nuc is a nucleoside moiety having a 5'-terminal and a 3'-terminal;

Q1 is a 5'-phosphate group,

Q2 is a 3'-phosphate group;

Lnk is a linking group; and

Lbl is an observable label moiety.

In certain embodiments, a labeled nucleotide composition in accordance with the present invention is a salt, conjugate base, tautomer, or ionized form of a composition having structure (I).

Nuc is a nucleoside moiety having a 5'-terminal and a 3'-terminal; the nucleoside moiety may be any moiety having at least one nucleoside subunit, e.g. at least two nucleoside subunits, at least 3 nucleoside subunits, at least 5 nucleoside subunits, at least 10 nucleoside subunits, and up to about 100 bases long, or longer. In certain embodiments, the nucleoside moiety will be less than 50 bases long, e.g. less than 40 bases long, less than 30 bases long, less than 20 bases long. In particular embodiments, the nucleoside moiety Nuc is an oligonucleotide moiety having a 5'-terminal and a 3'-terminal.

The 5'-phosphate moiety Q1 is attached to the nucleoside moiety Nuc via the 5'-terminal of the nucleoside moiety (e.g. at the terminal 5' carbon of the nucleoside moiety). The nucleoside moiety is attached to the 5'-phosphate moiety via an oxygen of the 5'-phosphate moiety.

The 3'-phosphate moiety Q2 is attached to the nucleoside moiety Nuc via the 3'-terminal of the nucleoside moiety (e.g. at the terminal 3' carbon of the nucleoside moiety). The nucleoside moiety is attached to the 3'-phosphate moiety via an oxygen of the 3'-phosphate moiety.

As described above with regard to structure (I), the Nuc group is a nucleoside moiety having a sugar group bound to a purine or pyrimidine base. The sugar group of the nucleoside moiety may be any sugar group known in the art of polynucleotides and polynucleotide analogues. Representative sugar groups may be selected from monosaccharides, ketoses, aldoses, pentoses (five carbon sugars), hexoses (six carbon sugars), including any such groups modified by e.g. oxidation, deoxygenation, introduction of other substituents, alkylation and acylation of hydroxyl groups, and chain branching. The sugar group is typically ribose or 2'-deoxyribose, although other sugars may be used. In an embodiment, the sugar is arabinose. The purine or pyrimidine base of the nucleoside moiety may be selected from the naturally occurring purine and pyrimidine bases, e.g., adenine (A), thymine (T), cytosine (C), guanine (G), or uracil (U), or modified purine and pyrimidine bases, and common analogs, e.g. such as are recited herein. Certain purine or pyrimidine analogs that are contemplated in this context include those described in U.S. pat. appl'n Ser. No. 10/324,409 entitled "Method of Producing Nucleic Acid Molecules with Reduced Secondary Structure", filed on Dec. 18, 2002, and also those described in U.S. pat. appl'n Ser. No. 09/358141 entitled "Method of Producing Nucleic Acid Molecules with Reduced Secondary Structure", filed on Jul. 20, 1999. In particular embodiments, the purine or pyrimidine base may have a protecting group, as is commonly known in the art of polynucleotide synthesis.

Still referring to structure (I), the linking group Lnk is selected from (1) a linking group linking the 3'-phosphate group Q2 and the observable label moiety Lbl; or (2) a covalent bond between the 3'-phosphate group Q2 and the observable label moiety Lbl (e.g. the observable label moiety Lbl is directly bound to an oxygen of the 3'-phosphate group Q2). In particular embodiments, the linking group Lnk may be any linking group via which the 3'-phosphate group Q2 is attached to the observable label moiety Lbl. The linking group Lnk is typically selected from (1) a lower alkyl group; (2) a modified lower alkyl group in which one or more linkages selected from ether-, thio-, amino-, oxo-, ester-, and amido- is present; (3) a modified lower alkyl substituted with one or more groups including lower alkyl; aryl, aralkyl, alkoxyl, thioalkyl, hydroxyl, amino, sulfonyl, halo; or (4) a modified lower alkyl substituted with one or more groups including lower alkyl; alkoxyl, thioalkyl, hydroxyl, amino, sulfonyl, halo, and in which one or more linkages selected from ether-, thio-, amino-, oxo-, ester-, and amido- is present. The linking group Lnk may be bonded to the adjacent 3'-phosphate group Q2 at any position of the linking group Lnk available to bind to the adjacent 3'-phosphate group Q2. Similarly, the linking group Lnk may be bonded to the adjacent observable label moiety Lbl at any position of the linking group Lnk available to bind to the adjacent observable label moiety Lbl. In certain embodiments, the linking group Lnk is a single methylene group, e.g. —CH$_2$—, or may be an alkyl group or modified alkyl group up to about 24 carbons long (and which may be straight-chain or branched-chain). In certain such embodiments, one or more linkages selected from ether-, oxo-, thio-, and amino- is present in the straight- or branched chain modified alkyl group. In an embodiment, the linking group Lnk comprises optionally substituted ethoxy, propoxy, or butoxy groups (i.e. may include the structure —{(CH$_2$)$_m$—O}$_n$—, wherein m is a integer selected from 2, 3, 4, and n is a integer selected from 1, 2, 3, 4, 5, 6). In an embodiment, the linking group Lnk has the structure —(CH$_2$)$_m$-Lkg-(CH$_2$)$_n$—, wherein m and n are integers independently selected from the range of 1 to about 12, e.g. from the range of 2 to about 8, and Lkg is a linkage selected from ether-, thio-, amino-, oxo-, ester-, and amido-. In an example, Lnk has the structure —(CH$_2$)$_m$—NH—C(O)—(CH$_2$)$_n$—, wherein m and n are integers independently selected from the range of 1 to about 12, e.g. from the range of 2 to about 8, e.g. from the range of 3 to about 6; in a particular embodiment, m is 6 and n is 5.

In particular embodiments, the linking group Lnk has a first terminal site and a second terminal site. In such embodiments, the linking group Lnk is bound to the 3'-phosphate Q2 at the first terminal site and the linking group Lnk is bound to the observable label moiety Lbl at the second terminal site. The first and second terminal sites will depend on the design of the linking group taking into consideration, for example, the method used to attach the observable label moiety to the rest of the labeled nucleotide composition.

Thus, in particular embodiments of the invention, the labeled substrate has a nucleotide moiety having a terminal 3'-phosphate group and an observable label moiety bound to the nucleotide moiety via a linking group attached to the terminal 3'-phosphate group.

The observable label moiety is a moiety that provides for an observable signal that indicates the presence of the observable label moiety. Typical examples include a chromogenic moiety, a fluorophore, a mass label, a spin label, a radiolabel, or other labels known in the art. In particular embodiments, the observable label moiety is a fluorophore selected from the group consisting of Cy3, Cy5, and an Alexa dye. Further examples of label moieties include any commercially available fluorophores that can be conjugated to mononucleotides or polynucleotides, e.g. dyes from Molecular Probes (Eugene, Oreg. and Leiden, The Netherlands) such as the Alexa Fluor series (example: Alexa 350, Alexa 430, Alexa 532, Alexa 546, Alexa 568, and Alexa 594) and the series of BODIPY conjugates. Other examples include: Tamra, Fluorescein, carboxyfluorescene, JOE, rhodamine, carboxyrhodamine, CY series, Oyster series. More information about commercially available dyes for oligonucleotide conjugation can be found at the website accessed by typing "www" followed by ".synthegen.com" into the address bar of a typical internet browser. Any such dyes may potentially be used in accordance with the methods described herein. Although the examples described herein use a fluorophore as the label, it will be apparent to those of ordinary skill that other labels may be used (instead of a fluorophore, or even in addition to a fluorophore). Such labels typically are well known in the art.

The observable label moiety may be any observable moiety that is compatible with the ligation reaction. In other words, the label moiety should not prevent the ligation reaction, e.g. by interfering with the enzyme having an RNA ligation activity. In embodiments such as illustrated in FIG. 1, the label moiety may be attached to a mononucleotide moiety via the terminal 3'-phosphate at the end of the mononucleotide moiety or may be attached to an oligonucleotide moiety via the terminal 3'-phosphate at the end of the oligonucleotide moiety. The observable label moiety could be incorporated as a special phosphoramidite during the oligoribonucleotide synthesis or as a post-synthetic modification. An example of the phosphoramidite method includes direct coupling of label-containing phosphoramidite during synthesis of the oligonucleotide moiety, or the incorporation of amino-activated phosphoramidite during synthesis of the oligonucleotide moiety, which enables post-synthetic coupling to desired observable label moiety. In particular embodiments, the observable label moiety is attached to the nucleotide moiety via a linking group, wherein the linking group may be attached to the nucleotide moiety via a 3' terminus of the nucleotide moiety. The linking group may be any linking group known in the art that does not prevent the ligation reaction (e.g. does not prevent the enzyme having an RNA ligation activity from ligating the RNA and the labeled substrate). Any such linking groups or other means of attachment of the label moiety to the nucleotide moiety known in the art may provide for the labeled substrate.

Thus, in particular embodiments, the labeled substrate has the structure:

N-D wherein: N is selected from a mononucleotide moiety or an oligonucleotide moiety having a length of less than about 100 bases, wherein N has a terminal 3'-phosphate group, and D is an observable label moiety attached to N via the terminal 3'-phosphate group of N.

An embodiment of a method in accordance with the present invention is illustrated in FIG. 1. In FIG. 1, the method 100 of labeling RNA includes heating 104 the sample (which includes the RNA 102) in the presence of DMSO 105. The solution is then snap-cooled 106, quickly lowering the temperature, e.g. to less than about 5° C. The labeled substrate 110A or 110B may then be added 108 to the resulting cooled solution (containing the DMSO and the RNA 102 from the sample). The labeled substrate 110A or 110B typically is a mononucleotide with a 3' fluorophore and 5' phosphate 110A, or an oligonucleotide with a 3' fluorophore and 5' phosphate 110B. The enzyme having an RNA ligation activity 114 is also added 112. In typical embodiments, the concentrations of the solutions and the volumes added are planned to provide that the resulting solution has the desired concentration of DMSO (e.g. in the range of about 20% to about 30%, more typically in the range of about 22% to about 28%, even more typically in the range of about 24% to about 26%). The resulting solution is then allowed to react 116 under conditions and for a time sufficient for the coupling of the labeled substrate to the RNA to occur, thereby providing the labeled RNA 118A or 118B. Typical conditions 120 of overnight incubation at 16° C. are shown for the embodiment of FIG. 1, although these conditions may vary depending on the particular enzyme used and the RNA and labeled substrate provided. In the illustrated embodiment, the label is a fluorophore 111, but other labels may be used as long as the coupling of the labeled substrate to the RNA may still occur. Selection and optimization of the conditions is within routine experimentation for one of ordinary skill in the art given the disclosure herein.

In particular embodiments, the enzyme having an RNA ligation activity catalyzes a coupling reaction between a donor molecule having a 5'-phosphate and an acceptor molecule having a 3'-hydroxyl, as shown in the reaction:

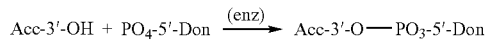

Where:
Acc-3'-OH is the acceptor molecule having a 3'-hydroxyl;
PO$_4$-5'-Don is the donor molecule having a 5'-phosphate;
Acc-3'-O—PO$_3$-5'-Don is the product having the coupled donor and acceptor moieties (e.g. the labeled RNA); and
(enz) is the enzyme having an RNA ligation activity.

In certain embodiments, such as that illustrated in FIG. 1, the acceptor molecule is the RNA 102 and the donor molecule is the labeled substrate 110A or 110B. The resulting product 118A or 118B has the labeled substrate moiety downstream from the RNA, i.e. the product is a downstream labeled RNA. Thus, based upon selection of the RNA and labeled substrate as disclosed herein, methods in accordance with the present invention result in downstream labeled RNA.

It should be noted that the general utility of the method is not limited to the particular sequence of steps shown in the figures. Other sequences of steps leading to essentially similar results are intended to be included in the invention. For example, in certain embodiments, the labeled substrate may be dissolved in a solution that includes the DMSO, and the resulting solution mixed with the sample prior to contacting with the enzyme having an RNA ligase activity. Thus, in particular embodiments, the invention includes any process which results in contacting the sample with the enzyme having an RNA ligation activity in the presence of the labeled substrate under conditions which include a DMSO concentration in the range from about 20% to about 30%.

With reference to FIG. 1, in certain embodiments before the enzyme having an RNA ligation activity 114 is added 112, the method 100 includes heating 104 the solution containing the DMSO 105 and the RNA 102 from the sample. In this optional heating step, the RNA is typically heated to a temperature of at least about 70° C. (e.g. at least about 80° C., at least about 85° C., at least about 90° C., at least about 95° C.; and up to about 105° C. or 110° C.) under conditions that include a DMSO concentration of at least about 35% DMSO, e.g. at least about 40% DMSO (typically up to about 60% DMSO, although in some embodiments the DMSO concentration may be up to 70% DMSO, up to 80% DMSO, or even more). This optional heating is maintained for at least 10 seconds, typically at least about 20 seconds, at least about 30 seconds, at least about 1 minute, at least about 2 minutes, and up to about 15 minutes, or more. In particular embodiments, reaction solutions of up to about 50 microliters are heated for about 30 to about 60 seconds per 5-10 microliters of reaction solution. After the heating, the RNA is typically quickly cooled (e.g. to less than about 40° C., more typically less than about 20° C., or in some embodiments less than about 5° C.) before adding the enzyme having an RNA ligation activity. In typical embodiments, the RNA sample is maintained at the cool temperature for at least 1 minute, more typically at least 2 minutes, e.g. at least 5 minutes, and up to 15 minutes or more, e.g. up to 30 minutes or more, such as until the RNA sample is needed for the next steps in the method. In certain embodiments, the heating and cooling steps are optional and may be omitted.

It should be noted that, in particular embodiments, the RNA in the sample is isolated via a process that results in the RNA in the sample having a 5'-phosphate. For embodiments such as that pictured in FIG. 1, in which the RNA in the sample does not have a 5'-phosphate, a preparatory treatment of subjecting the RNA in the sample to a dephosphorylation reaction is conducted prior to labeling the RNA in the sample by the ligation method illustrated in FIG. 1. Such dephosphorylation reactions are well known in the art, for example, treating the RNA sample with an enzyme having a 5'-phosphatase activity, e.g. calf intestine alkaline phosphatase, shrimp alkaline phosphatase, or *E. coli* alkaline phosphatase, or any other method of dephosphorylating the RNA known in the art. Thus, in certain embodiments, the method of labeling RNA in a sample includes, prior to contacting the sample with the enzyme having an RNA ligation activity, contacting the sample with an enzyme having a 5'-phosphatase activity to remove 5'-phosphate groups from the RNA in the sample.

In some embodiments, the labeled substrate has only one observable label moiety attached to the nucleotide moiety. In such embodiments, the labeled RNA will consist essentially of RNA labeled with a single label moiety (i.e. each labeled RNA molecule will have only one observable label moiety attached—referenced herein as "singly-labeled RNA"). This potentially provides increased ease of use in quantitative methods using the labeled RNA.

In other embodiments, the nucleotide moiety of the labeled substrate has a plurality of observable label moieties. In such embodiments, when the labeling reaction is performed to yield the labeled RNA, each labeled RNA molecule will have a plurality of observable label moieties (referenced herein as "multiply-labeled RNA"). Thus, the labeled RNA will consist essentially of RNA labeled with a plurality of label moieties. This increased labeling of the RNA may provide for greater sensitivity in analyses using the labeled RNA. In particular embodiments, each labeled RNA molecule in the sample will be labeled with a consistent number of observable label moieties (relative to the other labeled RNA molecules in the sample). This provides opportunity for more quantitative analysis of labeled RNA than in methods that provide an inconsistent number of observable labels per labeled RNA molecule.

In certain embodiments, methods of performing an array analysis of an RNA sample are provided. In certain embodiments, the invention provides a method of performing an array analysis wherein the method includes labeling the RNA in the sample to provide labeled RNA using a labeling method in accordance with the methods described herein. The labeled RNA is then contacted with an array under conditions sufficient to provide for specific binding of labeled RNA to the array. The array typically is then interrogated to provide data on binding of the labeled RNA to the array.

Standard hybridization techniques (using stringent hybridization conditions) are used to hybridize a labeled sample to a nucleic acid array. Suitable methods are described in references describing CGH techniques (Kallioniemi et al., Science 258:818-821 (1992) and WO 93/18186). Several guides to general techniques are available, e.g., Tijssen, Hybridization with Nucleic Acid Probes, Parts I and II (Elsevier, Amsterdam 1993). For descriptions of techniques suitable for in situ hybridizations, see Gall et al. Meth. Enzymol., 21:470-480 (1981); and Angerer et al. in Genetic Engineering: Principles and Methods (Setlow and Hollaender, Eds.) Vol 7, pgs 43-65 (Plenum Press, New York 1985). See also U.S. Pat. Nos: 6,335,167; 6,197,501; 5,830,645; and 5,665,549; the disclosures of which are herein incorporated by reference. Hybridizing the sample to the array is typically performed under stringent hybridization conditions, as described herein and as known in the art. Selection of appropriate conditions, including temperature, salt concentration, polynucleotide concentration, time(duration) of hybridization, stringency of washing conditions, and the like will depend on experimental design, including source of sample, identity of capture agents, degree of complementarity expected, etc., and are within routine experimentation for those of ordinary skill in the art to which the invention applies.

Following hybridization, the array-surface bound polynucleotides are typically washed to remove unbound and not tightly bound labeled nucleic acids. Washing may be performed using any convenient washing protocol, where the washing conditions are typically stringent, as described above.

Following hybridization and washing, as described above, the hybridization of the labeled target nucleic acids to the capture agents is then detected using standard techniques of reading the array, i.e. the array is interrogated. Reading the resultant hybridized array may be accomplished by illuminating the array and reading the location and intensity of resulting fluorescence at each feature of the array to detect any binding complexes on the surface of the array. For example, a scanner may be used for this purpose, which is similar to the AGILENT MICROARRAY SCANNER available from Agilent Technologies, Palo Alto, Calif. Other suitable devices and methods are described in U.S. patent applications: Ser. No. 09/846,125 "Reading Multi-Featured Arrays" by Dorsel et al.; and U.S. Pat. No. 6,406,849. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). In the case of indirect labeling, subsequent treatment of the array with the appropriate reagents may be employed to enable reading of the array. Some methods of detection, such as surface plasmon resonance, do not require any labeling of nucleic acids, and are suitable for some embodiments.

Results from the reading or evaluating may be raw results (such as fluorescence intensity readings for each feature in one or more color channels) or may be processed results (such as those obtained by subtracting a background measurement, or by rejecting a reading for a feature which is below a predetermined threshold, normalizing the results, and/or forming conclusions based on the pattern read from the array (such as whether or not a particular target sequence may have been present in the sample, or whether or not a pattern indicates a particular condition of an organism from which the sample came).

In certain embodiments, results from interrogating the array are used to assess the level of binding of the population of labeled nucleic acids to capture agents on the array. The term "level of binding" means any assessment of binding (e.g. a quantitative or qualitative, relative or absolute assessment) usually done, as is known in the art, by detecting signal (i.e., pixel brightness) from a label associated with the sample nucleic acids, e.g. the digested sample is labeled. The level of binding of labeled nucleic acid to capture agent is typically obtained by measuring the surface density of the bound label (or of a signal resulting from the label).

In certain embodiments, a surface-bound polynucleotide may be assessed by evaluating its binding to two populations of nucleic acids that are distinguishably labeled. In these embodiments, for a single surface-bound polynucleotide of interest, the results obtained from hybridization with a first population of labeled nucleic acids may be compared to results obtained from hybridization with the second population of nucleic acids, usually after normalization of the data.

The results may be expressed using any convenient means, e.g., as a number or numerical ratio, etc.

EXAMPLES

The practice of the present invention will employ, unless otherwise indicated, conventional techniques of synthetic organic chemistry, biochemistry, molecular biology, and the like, which are within the skill of the art. Such techniques are explained fully in the literature. Unless otherwise defined herein, all technical and scientific terms used herein have the same meaning as commonly understood by one of ordinary skill in the art to which the invention belongs.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

Experimental Methods

RNA ligation was assessed with synthetic RNA oligonucleotides (21-23 nucleotides, Dharmacon) in reaction solutions containing 0, 15, 20, 25, and 30% DMSO. The reactions containing 25% DMSO were assayed with and without the pre-heating step. Stock solutions of 20 μM RNA oligonucleotides were stored in 1×TE (10 mM Tris-HCl, pH 7.5, 1 mM EDTA). Initial mixtures of RNA, DMSO and water were first assembled. For pre-heated samples, the heated mixture contained 40-70% DMSO and were heated using a 104° C. heating block for 1.5-2 minutes. The heated samples were immediately set on ice for >5 minutes prior to final assembly. The final reaction contains 1× Amersham Pharmacia RNA ligase buffer (50 mM Tris-HCl, pH 7.5, 10 mM $MgCl_2$, 10 mM DTT, 1 mM ATP, 60 ng/μL BSA) 1 unit/μL T4 RNA ligase, 100 μM, 5'-phosphate-cytidyl-phosphate-Cy5-3' (pCpCy5) or 5'-phosphate-cytidyl-phosphate-Cy3-3'(pCpCy3) (Dharmacon) and 2-4 μM RNA oligonucleotides. The reactions were incubated at 16° C. overnight. RNA ligase was inactivated by heating the reaction solutions using a 104° C. heating block for 1.5-2 minutes, followed by immediately setting on ice for >5 minutes.

The labeling efficiency was determined by 5'-phosphorylation of RNA ligation reaction aliquots with radioactive $P^{32}$-gamma-ATP. The resulting mixture was desalted with Micro Bio-Spin™ (BioRad) desalting columns. The desalted mixture was loaded onto denaturing polyacrylamide gel. Since the ligation products contain an extra nucleotide and fluorophore, they have a lower electrophoretic migration rate than the unligated precursors. $P^{32}$-labeled RNA bands are visualized and quantified with phosphorimager (Molecular Dynamics). The ligation efficiency was determined by the ratio of ligated vs. unligated $P^{32}$-labeled RNA bands. Thus, ligation efficiency may be expressed as the mol % of initial RNA that winds up having an attached label moiety.

All water used in the studies presented here are non-DEPC treated RNase-free water for DEPC treated water can decrease reaction efficiency. Labeling efficiency was first optimized with synthetic miRNAs using T4 RNA ligase (Amersham cat# E2052Y) at 16° C. overnight. The 10 uL labeling reaction contained 20 pmol synthetic miRNA, 4 u T4 RNA ligase, using the manufacturer's 10× T4 RNA Ligase buffer (1× concentration: 40 mM Tris-HCl, pH 7.5, 10 mM $MgCl_2$, 10 mM DTT, 1 mM ATP), 0.01% BSA, 1 nmol pCp-Cy5 or pCp-Cy3 and 0, 15, 25, or 30% (v/v) DMSO (Sigma). The pCp-Cy5 and -Cy3 were made by conjugating Cy5 or Cy3 (Amersham) to the 3'phosphate of pCp (Dharmacon). For the pre-heated samples, RNA was first combined with DMSO and water to 6 uL, heated at 100° C. for 1 minute, immediately cooled to 0° C. in an ice water bath prior to assembly of the other components. To quantify pCp-Cy labeling yield, 1/10 of the ligase reaction mixture was labeled with $^{32}$P using T4 polynucleotide kinase as previously described (Wang, Di Gate & Seeman, "An RNA Topoisomerase", Proc. Natl. Acad. Sci., USA (1996) 93, 9477-9482), analyzed on a denaturing 20% polyacrylamide gel (19:1 acrylamide: bisacrylamide, 50% w/v urea, 89 mM tris-borate, 2 mM EDTA, 55° C.), and quantitated by a phosphorimager (Molecular Dynamics).

For RNA samples isolated from tissue, 120 ng of tissue total RNA (Ambion), 60 ng of fractionated tissue RNA (Ambion), or 120 ng of preserved tumor RNA (Michael Bittner, Translational Genomics Research Institute) was dephosphorylated with 16 u calf intestine alkaline phosphatase (Amersham cat# E2250Y) in manufacturer's supplied buffer (1× concentration: 50 mM Tris-HCl, pH 9.0, 1 mM MgCl2) in 10 uL for 30 minutes at 37° C. When spike-in synthetic RNAs are used, 0.2 amol to 0.2 fmol of two or more of the *Drosophila* miRNAs (dme-miR-31a, -285, -6, and -3) were added to the total RNA mixture. The reaction was terminated by heating at 100° C. for 5 minutes followed by immediate cooling to 0° C. in an ice water bath. 7 uL of DMSO was added to the 10 uL inactivated phosphatase reaction sample and heated to 100° C. for 3 minutes, followed by immediate cooling to 0° C. with an ice water bath. 2.8 uL each of 10× T4 RNA ligase buffer and 0.1% BSA were added to the sample. Ligation was performed with 50 uM pCp-Cy5 or -Cy3 and 15 u T4 RNA ligase in 28 uL at 16° C. overnight.

The relative abundance of the miRNAs from tissue total RNAs was reproducible when labeled with excess pCp-Cy5 or Cy3 (1.4-8.4 nmol pCp-Cy per 120-240 total RNA), independent of the RNA quantity (60-240 ng total RNA/array), the phosphatase used, the ligase quantity (0.4-4 u/uL reaction), and the reaction volume (10-28 uL). The optimum signal strength and consistency was observed using 16 u calf intestine alkaline phosphatase, 10-30 u T4 RNA ligase reaction, and 50-300 uM pCp-Cy per 28 uL reaction containing 120-240 ng total RNA.

Description of Experiments

In the experiments described here, T4 RNA ligase is used to label synthetic RNA oligonucleotides with 5'-phosphate-cytidyl-phosphate-Cy5-3' (pCpCyS) or 5'-phosphate-cytidyl-phosphate-Cy3-3'(pCpCy3). The reaction conditions described here have been observed to result in ligation efficiencies of about 60% or more, e.g. about 70% or more, or 80% or more, up to about 95% or more, e.g. up to about 99% with minimal sequence discrimination. This was accomplished by reacting at 25% DMSO, 16° C. overnight, with donor to acceptor ratio of >12.5:1. The reaction buffer contains 50 mM Tris-HCl, pH 7.5, 10 mM MgCl2, 10 mM DTT, 1 mM ATP, 60 µg/mL BSA, and 25% DMSO. Typical reactions are 10 µL with 2 µM RNA, 100 µM pCpCy5 or pCpCy3, and 4 units T4 RNA ligase (Amersham/Pharmacia). Reaction efficiency seemed unaffected by increasing the RNA concentration to 8 µM or decreasing enzyme to 2 units.

The labeling efficiency was determined by first performing the ligation reaction. An aliquot of the ligation mixture was then labeled on the 5' end with radioactive $P^{32}$-γ-ATP and T4 Polynucleotide Kinase. The control sample, which did not undergo ligation reaction, and final reaction mixture was denatured with formamide and assessed with denaturing polyacrylamide gel electrophoresis (1× or 0.5×TBE, 50% urea, 15-20% polyacrylamide with 19:1 acrylamide to bisacrylamide ratio, at about 50° C.). The resulting gel was scanned with Molecular Dynamics Storm Phosphorimager for pCpCy5-labeled RNA. The ligation product was clearly visible as a red fluorescent miRNA. The gel was then exposed to phosphor screen to determine the pCpCy5-labeling efficiency. Since the addition of pCpCy5 increases the acceptor miRNA by 1 nucleotide and a fluorophore, the mobility of the cy5-labeled strand was lower than the unreacted strand. They appear as distinct bands when scanned in the phosphor mode on the phosphoimager; this was further verified by the relative mobility between the ligase reacted samples and unreacted controls (both the ligase reacted samples and the unreacted controls were labeled with $P^{32}$-γ-ATP). Thus the relative level of radioactivity between the Cy-labeled and unlabeled bands reveals the ligation efficiency. The reaction efficiency of pCpCy3 was determined similarly except the Cy3 labeled strand was undetectable by the fluorescent mode of the phosphorimager. The product and reactant miRNA bands of the Cy3 reaction were defined by the mobility of Cy5 reactions in polyacrylamide gel electrophoreseis and phosphorimager analysis.

Ligation efficiency under different reaction conditions was extensively tested with pCpCy5 and 4 separate synthetic oligonucleotides (SEQ ID NOs:1-4), each of which contains the same sequence as *drosophila* miRNA (as indicated):

TABLE 1

Test Sample miRNAs

| SEQ ID NO: | Name | Sequence | 3' Terminal NT | #NT |
|---|---|---|---|---|
| 1 | dme-miR-3 | UCACUGGGCAAAGUGUGUCUCA | A | 22 |
| 2 | dme-let-7 | UGAGGUAGUAGGUUGUAUAGU | U | 21 |
| 3 | dme-miR-14 | UCAGUCUUUUUCUCUCUCCUA | A | 21 |
| 4 | dme-miR-31a | UGGCAAGAUGUCGGCAUAGCUGA | A | 23 |

These miRNAs were labeled with 80-99% efficiency when the reaction mixture contained 95% (molar ratio) competitors composing of other miRNAs and longer single stranded RNAs (100-500 nts). Thus it is reasonable to expect high labeling efficiency in heterogeneous biological RNA mixtures.

After optimization of labeling efficiencies of these RNAs with Cy5, the labeling reaction was expanded to include the following sequences (SEQ ID NOs:6-10) with pCpCy5 and pCpCy3 in separate studies. These additional strands address any bias that may result from 3' terminal nucleotide, potential secondary structures and nucleotide content of the miRNA.

TABLE 2

Additional Test Sample miRNAs

| SEQ ID NO: | Name | Sequence | 3' Terminal NT | #NT |
|---|---|---|---|---|
| 5 | dme-miR-2b | UAUCACAGCCAGCUUUGAGGAGC | C | 23 |
| 6 | dme-miR-6 | UAUCACAGUGGCUGUUCUUUUU | U | 22 |

TABLE 2-continued

Additional Test Sample miRNAs

| SEQ ID NO: | Name | Sequence | 3' Terminal NT | #NT |
|---|---|---|---|---|
| 7 | dme-miR-184* | CCUUAUCAUUCUCUCGCCCCG | G | 21 |
| 8 | dme-miR-285 | UAGCACCAUUCGAAAUCAGUGC | C | 22 |
| 9 | dme-miR-308 | AAUCACAGGAUUAUACUGUGAG | G | 22 |
| 10 | dme-miR-316 | UGUCUUUUUCCGCUUACUGGCG | G | 22 |

Potentially, the RNA ligase method can be used for dyes other than Cy5 and Cy3, but the efficiency may differ from the ones presented here. Moreover, it is possible to determine the labeling efficiencies of each individual miRNA of a given set and perform highly quantitative microarray experiments by correlating fluorophore counts with number of molecule. For example, in an array hybridization experiment wherein an array is contacted with a labeled RNA sample, it is possible to ascertain the total quantity of fluorophores in a given area of the array by interrogating (or scanning) the array; given the labeling efficiency of the labeled RNA sample (determined as disclosed herein), the quantity of RNA hybridized to the given area of the array may be determined.

Figure 2:
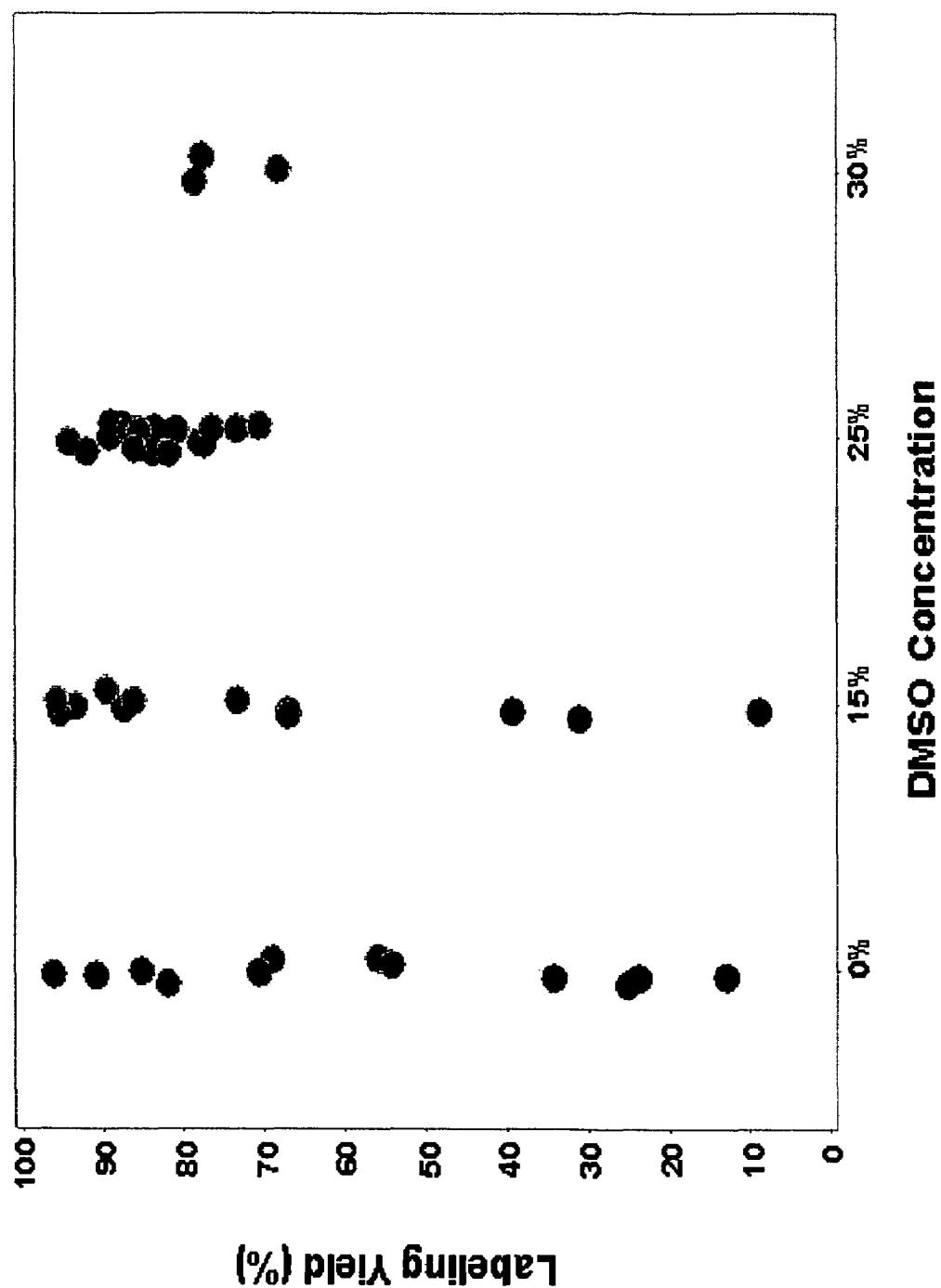
FIG. 2 shows data from labeling reactions at various DMSO concentrations.

Quantitative direct labeling methods that minimize sample manipulations, such as size separation or amplification, are most likely to produce accurate measurement from mixed RNA samples, e.g. to obtain miRNA profiles from isolated miRNA samples. The small mature miRNA is an ideal substrate for T4 RNA ligase, though this enzyme can be sensitive to RNA sequence and secondary structures (England & Uhlenbeck, Biochemistry (1978) 17: 2069; Romaniuk et al., 1982; Romaniuk & Uhlenbeck, Meth. Enzymol. (1983) 100: 52). To minimize the effect of structure and sequence differences among miRNAs, dimethylsulfoxide (DMSO), which is an effective RNA denaturant (Strauss et al., 1968), is added to the reaction solution. Up to 15% DMSO has been reported to stimulate T4 RNA ligase activity (Romaniuk & Uhlenbeck, 1983). By attaching a single cyanine dye to the 3' phosphate of 3',5'-cytidine bisphosphate (pCp-Cy5 or pCp-Cy3), successful ligation produces a miRNA with an additional 3'cytidine and exactly one cyanine dye on its 3'end. Given that the approximate labeling efficiency may be determined (as described herein), in particular embodiments the present invention thus provides quantitative methods of performing array hybridization experiments. It is expected that this will provide a more sensitive assay system for the detection of variations of miRNA, such as found in developmental stages, tissue samples, disease states, as well as any individual and/or abnormal variations. Moreover, if more viral miRNAs are identified, this can become a novel diagnostic tool for active as well as latent viral infections In order to determine the optimal DMSO concentration, DMSO was titrated into the ligation reaction. Several synthetic RNA oligonucleotides were labeled in the presence of 0, 15, 25, and 30% DMSO, with and without pre-denaturation by heating and flash-cooling the RNA. Significant improvement in ligation yields was observed for 0 and 15% DMSO with pre-denaturation by heating. At 25% DMSO, similar yields were obtained with or without pre-denaturation, indicating a disruption of RNA secondary structure. FIG. 2 illustrates results obtained as follows: Five synthetic miRNAs containing different sequences were either directly labeled (blue) or heated prior to labeling (red) at 0, 15, 25, or 30% DMSO. At 25% DMSO, high labeling yields were observed independent of heat denaturation. Fifty-five separate reactions are shown.

Figure 3:
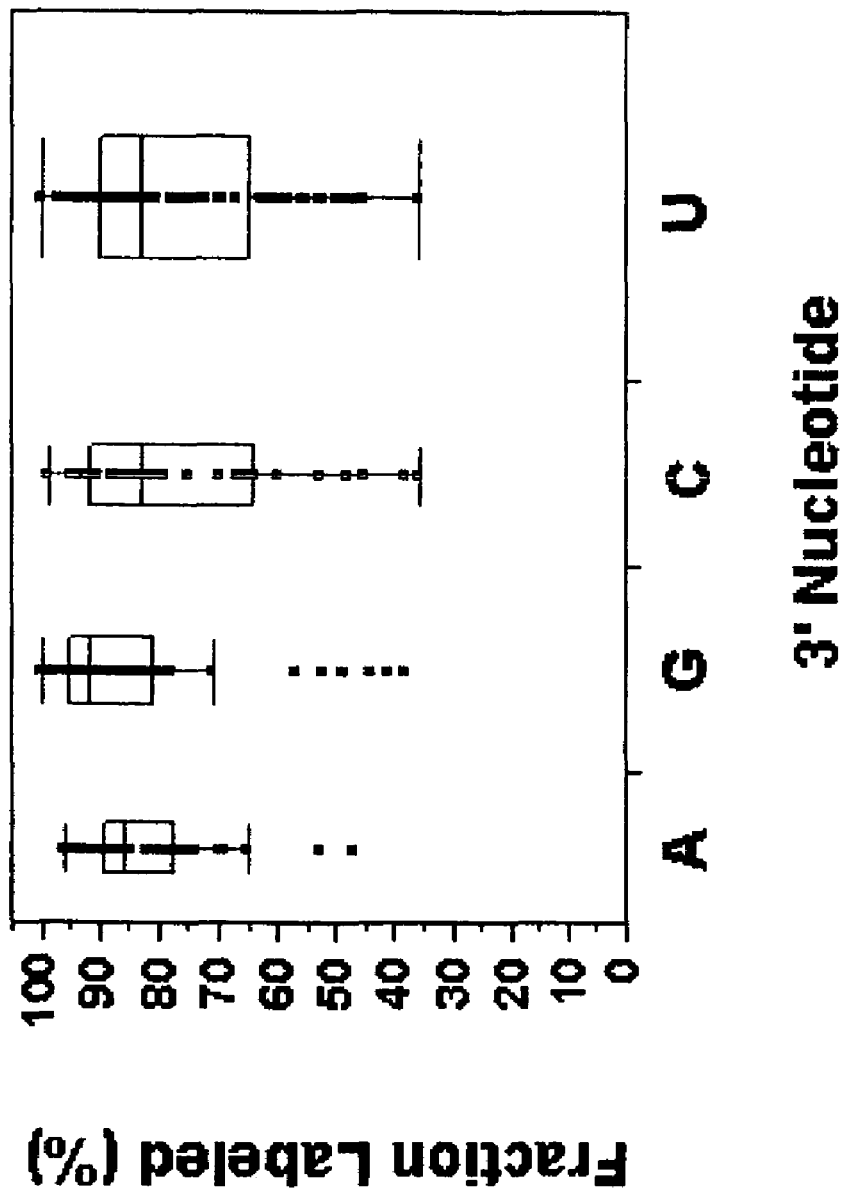
FIG. 3 shows yield data from labeling of various RNA samples.

When 53 individually labeled synthetic miRNAs were labeled in the presence of 25% DMSO, a slight 3'nucleotide sequence bias was observed. FIG. 3 shows box plots of labeling efficiencies of 53 different synthetic miRNAs. Results from 223 separate miRNA ligations are shown, categorized according to 3'nucleotide. The mean percent yields of the labeled product and the standard errors were 82±3 for A, 86±2 for C, 78±2 for G, and 78±2 for U. ANOVA p-value distinguishing the four distributions was 0.015, indicating that the labeling bias, while slight, is statistically significant. Ligations with low yields (<70%) were not reproducible, as subsequent ligations generally resulted in significantly higher yields (>80%). High yields (>90%) were very reproducible. This slight sequence bias was significantly lower than the sequence bias reported earlier (England & Uhlenbeck, Biochemistry (1978) 17: 2069). The presence of a 10-fold excess of mixed competitor miRNAs did not affect labeling efficiency, and synthetic hairpin pre-miRNAs were not effectively labeled (data not shown).

Determination of Labeling Efficiency of miRNAs in Complex Samples:

RNA ligase is used to label a complex RNA mixture, such as the total RNA or isolated mixtures of small RNAs from biological samples. The labeled mixtures are run on denaturing polyacrylamide gel and Northern blots are performed of individual miRNAs with radioactive probes. The RNAs labeled by RNA ligase will have a lower mobility relative to its unlabeled counterpart. Thus each target sequence will run as a doublet when probed by Northern blot. The ratio of RNA species in these doublets reflects the molar ratio of the RNA ligase labeled vs. unlabeled RNA species.

Although synthetic miRNAs labeled with >80% yields, it is possible that these yields cannot be sustained in the presence of the complex RNA species present in biological samples. To address this possibility, 120-240 ng of total RNA from various human tissues were dephosphorylated and directly labeled with varying quantities of T4 RNA ligase (4-60 units) and pCp-dye (1-300 uM). Labeling efficiency was monitored by the microarray signals from pre- and post-label spiked-in synthetic miRNAs (0.2 amol to 2 fmol) and by the consistency of measured tissue miRNA profiles. Reproducible spike-in signals and miRNA profiles were observed when the pCp-dye exceeded 1.4 nmol (50 uM) and the T4 RNA ligase exceeded 10 units (data not shown). Hybridized signals generally increased with increasing pCp-dye concentration, but no significant increase was observed beyond 2.8 nmol (100 uM). Stable miRNA expression profiles were obtained even with incomplete labeling, consistent with independent, non-competitive labeling of the different sequences in the complex RNA mixture.

RNA Labeling and Hybridization:

All enzymes were from Amersham, and reactions were performed with supplied buffer and BSA, unless otherwise specified. The pCp-Cy5 and -Cy3 were made by conjugating Cy5 or Cy3 (Amersham) to the 3'phosphate of pCp (Dharmacon). Labeling efficiency was optimized with 20 pmol synthetic miRNAs using T4 RNA ligase, 1 nmol pCp-Cy5 or pCp-Cy3 and 0, 15, 25, or 30% (v/v) DMSO (Sigma) in 10 uL, which was then labeled with $^{32}P$ using T4 polynucleotide kinase, analyzed on a denaturing 20% polyacrylamide gel, and quantitated by phosphorimager (Molecular Dynamics).

For miRNA profiling, 120 ng of tissue total RNA, 60 ng of fractionated tissue RNA, or 120 ng of preserved tumor RNA was dephosphorylated with 16 u calf intestine alkaline phosphatase, 30 minutes, 37° C. The reaction was terminated at 100° C. for 5 minutes and immediately cooled to 0° C. 7 uL of DMSO was then added and heated to 100° C., 3 minutes, and immediately cooled to 0° C. Ligase buffer and BSA were added and ligation was performed with 50 uM pCp-Cy5 or -Cy3 and 15 u T4 RNA ligase in 28 uL at 16° C. overnight.

Microarray Hybridization:

The synthetic miRNA set forth above were either labeled with Cy5 or Cy3 and hybridized onto microarrays as follows:

Labeled miRNA were desalted with BioRad Micro Bio-Spin™ 6 (as directed by BioRad instructions) to remove free fluorescent tags. The desalted miRNA was added to solution containing water and carrier (25-mer DNA with random sequence). The solution was heated for approximately 1 minute per 10 ul solution at 100° C. and immediately placed on ice. After cooling, 2× Agilent Hyb Buffer (1225 mM LiCl, 300 mM Li-MES, pH 6.1, 12 mM EDTA, 3.0% (w/v) lithium dodecyl sulfate, 2.0% (w/v) Triton X-100) was added to the mixture and the viscous liquid was mixed carefully. The final solution contained 1×Hyb Buffer and 0.1 µg/µl random 25-mer. The concentration of miRNA was varied for different experiments.

Hybridization was performed with SureHyb hybridization chamber (Agilent Part Number:G2534A) and place on rotisserie of hybridization oven overnight. The hybridization temperature was tested at 50° C. and 60° C.

After hybridization was completed, the Sure-Hyb chamber complex was removed from the oven and immediately disassembled in Wash Buffer 1 (6×SSC, 0.005% Triton X-102) at room temperature. The microarray was transferred to a fresh wash chamber containing Wash Buffer 1 and washed by stirring for 10 minutes at room temperature. The microarray was then washed in Wash Buffer 2 (0.1×SSC, 0.005% Triton X-102) by stirring at room temperature for 5 minutes. The microarray was slowly lifted out of the wash chamber after washing and dried with nitrogen as needed. The microarrays were scanned with Agilent Scanner (Agilent Product Number: G2565BA) at 100% and 5% sensitivity settings. The scanned data was extracted with Agilent Feature Extraction Software (Agilent Product Number; G2567AA) and the green and red background-subtracted signals were evaluated for hybridization efficiency and specificity. Data was further analyzed using Spotfire software and Microsoft Excel.

The method described herein for labeling of mixed RNA samples (such as small RNA isolated from a biological source such as a tissue sample or cell culture sample) provides reduced sequence bias in the labeled mixed RNA samples. When used in combination with array analysis of the resulting labeled mixed RNA, the methods described herein provide for more accurate quantitative analysis of relative amounts of individual species of labeled RNAs in the labeled mixed RNA samples. This is the first study to illustrate the advantage of reduced sequence bias in labeling, especially as combined with array analysis of mixed RNA samples. Unlike previous studies, the labeled substrate used here has 3'-phosphate modification, wherein the 3'-phosphate is bound to an observable label moiety via a linker moiety. This is the first study to illustrate the ligation efficiency of such modified donors.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties, provided that, if there is a conflict in definitions, the definitions provided herein shall control.

What is claimed is:

1. A method of labeling miRNA comprising:
  a) heating a sample comprising a plurality of miRNAs isolated from a biological source to at least 70°C. in a solution containing at least 35% DMSO and then cooling the sample to less than 10°C.; and
  b) contacting said sample with an RNA ligase in the presence of a labeled substrate under conditions sufficient to result in coupling of the labeled substrate to the miRNA in the sample to provide labeled miRNA, the conditions including a DMSO concentration in the range from 20% to 30%, wherein the labeled substrate comprises a nucleotide moiety having a terminal 3'-phosphate group and an observable label moiety attached to the nucleotide moiety via a linking group bound to the terminal 3'-phosphate group.

2. The method of claim 1, wherein said heating a sample comprises:
  heating said sample to at least 80°C. in a solution containing at least 40% DMSO and then cooling the sample to less than 50°C.

3. The method of claim 2, wherein the duration of heating is in the range of 10 seconds to 15 minutes.

4. The method of claim 1, wherein the nucleotide moiety is selected from a mononucleotide moiety or an oligonucleotide moiety.

5. The method of claim 1, wherein the nucleotide moiety has a length in the range from 2 to about 50 bases.

6. The method of claim 1, wherein the observable label moiety is selected from a chromogenic moiety, a fluorophore, a mass label, a spin label, or a radiolabel.

7. The method of claim 1, wherein the linking group is selected from (1) a lower alkyl group; (2) a modified lower alkyl group in which one or more linkages selected from ether-, thio-, amino-, oxo-, ester-, and amido- is present; (3) a modified lower alkyl substituted with one or more groups including lower allcyl; aryl, arakyl, alkoxyl, thioalkyl, hydroxyl, amino, sulfonyl, halo; or (4) a modified lower alkyl substituted with one or more groups including lower alkyl; alkoxyl, thioalkyl, hydroxyl, amino, sulfonyl, halo, and in which one or more linkages selected from ether-, thio-, amino-, oxo-, ester-, and amido- is present.

8. The method of claim 1, wherein the labeled substrate comprises a single observable label moiety and the labeled miRNA consists essentially of singly-labeled miRNA.

9. The method of claim 1, wherein the labeled miRNA is at least 70% of the initial miRNA in the sample.

10. The method of claim 1, further comprising, prior to contacting the sample with an RNA ligase, contacting the sample with an enzyme having a 5'-phosphatase activity to remove 5'-phosphate groups from the miRNA in the sample.

11. The method of claim 1, wherein said RNA ligase is capable of coupling a species selected from the group consisting of a nucleotide having a 5' phosphate, an oligonucleotide having a 5' phosphate, and an RNA having a 5' phosphate to an oligonucleotide having a 3' hydroxyl.

12. A method of performing an array analysis comprising:
  labeling miRNA in a sample comprising a plurality of miRNAs isolated from a biological source using a method according to claim 1 to provide the labeled miRNA, contacting the labeled miRNA with an array under conditions sufficient to provide for specific binding of labeled miRNA to the array; and interrogating the array to provide data on binding of the labeled miRNA to the array.

13. A method of labeling miRNA comprising:
a) heating a sample comprising a plurality of miRNAs isolated from a biological source to at least 70°C. in a solution containing at least 35% DMSO and then cooling the sample to less than 10°C.; and
b) contacting said sample with an RNA ligase in the presence of a labeled substrate under conditions sufficient to result in coupling of the labeled substrate to the miRNA in the sample to provide labeled miRNA, the conditions including a DMSO concentration in the range from 20% to 30%, wherein the labeled substrate has the structure (I):

Q1-Nuc-Q2-Lnk-Lbl wherein:
Nuc is a nucleoside moiety having a 5'-terminal and a 3'-terminal;
Q1 is a 5'-phosphate group attached to the nucleoside moiety Nuc via the 5'-terminal of the nucleoside moiety,
Q2 is a 3'-phosphate group attached to the nucleoside moiety Nuc via the 3'-terminal of the nucleoside moiety;
Lnk is a linking group; and
Lbl is an observable label moiety.

* * * * *

UNITED STATES PATENT AND TRADEMARK OFFICE
CERTIFICATE OF CORRECTION

PATENT NO.        : 7,572,585 B2                                     Page 1 of 1
APPLICATION NO.   : 11/496831
DATED             : August 11, 2009
INVENTOR(S)       : Hui Wang It is certified that error appears in the above-identified patent and that said Letters Patent is hereby corrected as shown below:

In column 28, line 27, in Claim 2, delete "50 °C." and insert -- 5 °C. --, therefor.

Signed and Sealed this

Tenth Day of August, 2010

David J. Kappos
*Director of the United States Patent and Trademark Office*